(12) United States Patent
Rahman et al.

(10) Patent No.: US 9,335,235 B2
(45) Date of Patent: May 10, 2016

(54) EXHAUST GAS SAMPLING DEVICE

(71) Applicant: HORIBA, Ltd., Kyoto (JP)

(72) Inventors: Montajir Rahman, Kyoto (JP);
Masahiro Nakane, Kyoto (JP); Kenji Hara, Kyoto (JP); Shigeru Nakatani, Kyoto (JP)

(73) Assignee: HORIBA, LTD., Kyoto (JP)

( * ) Notice: Subject to any disclaimer, the term of this patent is extended or adjusted under 35 U.S.C. 154(b) by 158 days.

(21) Appl. No.: 13/767,443

(22) Filed: Feb. 14, 2013

(65) Prior Publication Data

US 2013/0209330 A1    Aug. 15, 2013

(30) Foreign Application Priority Data

Feb. 14, 2012    (JP) .................................. 2012-029921

(51) Int. Cl.
   *G01N 1/22*    (2006.01)
(52) U.S. Cl.
   CPC ............ *G01N 1/2247* (2013.01); *G01N 1/2258* (2013.01); *G01N 2001/2261* (2013.01)
(58) Field of Classification Search
   CPC ................... G01N 1/2247; G01N 2001/2261; G01N 1/2258; G01N 15/0656; G01N 15/06; F01N 11/00; F01N 2550/12; F01N 2550/00; F02D 41/2474
   USPC .......................................... 700/270; 422/527
   See application file for complete search history.

(56) References Cited

U.S. PATENT DOCUMENTS

| | | | |
|---|---|---|---|
| 3,793,887 A | 2/1974 | Anderson et al. | |
| 3,817,100 A | 6/1974 | Anderson et al. | |
| 5,196,170 A * | 3/1993 | Patashnick et al. | 422/83 |
| 7,334,401 B2 * | 2/2008 | Cheng | F01N 3/021 |
| | | | 204/421 |

(Continued)

FOREIGN PATENT DOCUMENTS

| | | |
|---|---|---|
| JP | 63-181848 U1 | 11/1988 |
| JP | 63-267422 | 11/1988 |

(Continued)

OTHER PUBLICATIONS

MEXA-1400QL-NX(http://www.horiba.com/jp/automotive-testsystems/products/emission-measurement-systems/analyticalsystems/ standard-emissions/details/mexa-1400ql-nx-11246/), Jan. 2011, 7 pages.

(Continued)

*Primary Examiner* — Shogo Sasaki
(74) *Attorney, Agent, or Firm* — Brooks Kushman P.C.

(57) ABSTRACT

An exhaust gas sampling device is intended to heat or cool a temperature of sampled exhaust gas flowing through a sampling line to a desired temperature in accordance with various exhaust gas conditions and usage conditions of the sampling line irrespective of a temperature of the exhaust gas flowing through an exhaust pipe, and includes the sampling line for sampling the exhaust gas to be introduced into an analyzing instrument; a plurality of heating parts provided along the sampling line from an upstream side to a downstream side for heating the exhaust gas flowing through the sampling line; and a temperature control part for individually setting set temperatures of the plurality of heating parts using the temperature of the exhaust gas in the exhaust pipe and a target temperature of the exhaust gas in an outlet side of the heating part located in the most downstream as parameters.

6 Claims, 5 Drawing Sheets

(56) References Cited

U.S. PATENT DOCUMENTS

| | | | |
|---|---|---|---|
| 7,574,895 B2 * | 8/2009 | Schnell | G01N 15/0656 73/28.01 |
| 7,644,609 B2 * | 1/2010 | Reutiman | G01N 15/0656 73/114.69 |
| 2007/0163233 A1 * | 7/2007 | Cheng | F01N 3/021 60/277 |

FOREIGN PATENT DOCUMENTS

| | | |
|---|---|---|
| JP | 64-001931 | 1/1989 |
| JP | 1-180635 | 12/1989 |
| JP | 07505218 | 8/1995 |
| JP | 08-226879 A | 9/1996 |
| JP | 2002-055029 | 2/2002 |
| JP | 2003-014625 A | 1/2003 |
| JP | 2003-121319 A | 4/2003 |
| JP | 2005-308710 A | 11/2005 |
| JP | 2010-185837 | 8/2010 |
| JP | 2010-223650 | 10/2010 |
| JP | 2010-236877 A | 10/2010 |
| JP | 2010-249643 | 11/2010 |
| JP | 2012-002799 A | 1/2012 |
| WO | 93-22654 | 11/1993 |

OTHER PUBLICATIONS

MEXA-1100QL-N20(http://www.horiba.com/jp/automotive-testsystems/products/emission-measurement-systems/analyticalsystems/standard-emissions/details/laser-spectroscopic-motor-exhaustgas-analyzer-mexa-1100ql-n2o-19571/) Jan. 2013, 7 pages.

MEXA-ONA-QL-NX(http://www.horiba.com/jp/automotive-testsystems/products/emission-measurement-systems/analyticalsystems/standard-emissions/details/laser-spectroscopic-motor-exhaustgas-analyzer-mexa-one-ql-nx-21427/) Sep. 2013, 6 pages.

Black F, Constant Volume Sampling System Water Condensation, SAE Technical Paper Series 940970 and English-Japanese translation, U.S., SAE International, Detroit, MI, Feb. 28, 1994, 32 pages.

Summary and Analysis of Comments on the Notice of Proposed Rulemaking for Emission Standards and Test Procedures for Methanol-Fueled Vehicles and Engines, U.S., Environment Protection Agency, Washington, D.C., Jan. 1989, 51 pages.

* cited by examiner

EXHAUST GAS SAMPLING DEVICE

CROSS-REFERENCE TO RELATED APPLICATION

This application claims priority to JP Application No. 2012-029921, filed on Feb. 14, 2012, the disclosure of which is incorporated in its entirety by reference herein.

1. Technical Field

The present invention relates to an exhaust gas sampling device for sampling exhaust gas from an exhaust pipe in which exhaust gas flows and introducing the sampling gas into an analyzing instrument.

2. Background Art

Conventionally, there has been used a urea SCR system as a system for reducing $NO_x$ contained in engine exhaust gas discharged from a diesel engine. This urea SCR system is configured to arrange a SCR catalyst in an exhaust pipe so that urea $((NH_2)_2CO)$ is injected to the upstream side of the corresponding SCR catalyst.

The urea injected into the exhaust pipe produces $NH_3$ due to a thermal decomposition reaction of $(NH_2)_2CO + H_2O \rightarrow 2NH_3 + CO_2$. Then, this $NH_3$ reacts with $NO_x$ by the SCR catalyst so that $NO_x$ is reduced to be $N_2$. In specific, there occurs a reduction reaction of $4NH_3 + 4NO + O_2 \rightarrow 4N_2 + 6H_2O$, $4NH_3 + 2NO_2 + O_2 \rightarrow 3N_2 + 6H_2O$ in the SCR catalysis.

In the above system, if the amount of urea injected to the exhaust pipe is excessive, $NH_3$ is to be exhausted to the downstream side of the SCR catalysis. Moreover, if the amount of urea injected to the exhaust pipe is too small, $NO_x$ contained in the exhaust gas is not sufficiently reduced in the SCR catalysis and the exhaust gas including $NO_x$ is exhausted to the downstream side. Therefore, it is necessary to optimize the amount of urea to be injected in the SCR catalysis. And in order to check whether or not the amount of urea of the urea SCR is optimized, it is necessary to perform the sampling of the exhaust gas that has passed through the SCR catalysis so that the amount of urea or amount of ammonia contained in the corresponding exhaust gas must be examined.

The conventional exhaust gas measurement system includes a sampling line for sampling the exhaust gas from the downstream side of the SCR catalysis and an $NH_3$ analyzer for measuring a concentration of ammonia contained in the exhaust gas sampled by the corresponding sampling line, whereby it is checked based on the concentration of ammonia obtained by the $NH_3$ meter whether or not the injection amount of urea is optimum.

However, the temperature of the exhaust gas flowing through the exhaust pipe is changed to various temperatures (for example, 100° C. to 500° C.) according to operation conditions of the engine, and the urea injected to the exhaust pipe is passed through the SCR catalysis without sufficiently performing the thermal decomposition and hydrolysis thereof in some cases. Therefore, although the urea is to be contained in the sampled exhaust gas, if ammonia is produced without sufficient thermal decomposition and hydrolysis of the urea, a proper injection amount of urea cannot be decided to be problematic.

Here, as disclosed in Patent Literature 1, in order not to absorb ammonia to the sampling line, or in order to prevent condensation of a predetermined component contained in the exhaust gas, the sampling line is heated or cooled to be a predetermined constant temperature in some cases.

However, in a case where the sampling line is heated to a constant temperature for preventing the absorption and condensation, due to limitations of a measurement temperature of an analyzing instrument connected to the sampling line or such as a setting temperature of such as a filter and an orifice provided in the sampling line, a predetermined component such as urea contained in the exhaust gas cannot be heated or cooled to the temperatures required for thermal decomposition or hydrolysis to be problematic. For example, in the case where the measurement temperature of the $NH_3$ analyzer connected to the sampling line is 113° C., when considering a case where the urea contained in the exhaust gas flowing through the sampling line is desired to be introduced into the $NH_3$ analyzer after performing the thermal decomposition or hydrolysis, in the case where the temperature of the sampled exhaust gas is 500° C., the urea is to be thermally decomposed or the like in a stage of cooling from 500° C. to 113° C. Meanwhile, in the case where the temperature of the sampled exhaust gas is lower than 113° C., the predetermined component of the exhaust gas cannot be thermally decomposed or the like merely by heating the corresponding exhaust gas to be 113° C. to be problematic.

CITATION LIST

Patent Literature

Patent Literature 1: JP2010-236877A

SUMMARY OF INVENTION

Technical Problem

Therefore, the present invention has its essential object to make it possible to heat or cool a temperature of sampled exhaust gas flowing through a sampling line to be a desired temperature in accordance with such as various exhaust gas conditions and usage conditions of the sampling line irrespective of a temperature of the exhaust gas flowing through an exhaust pipe.

Solution to Problem

That is, an exhaust gas sampling device according to the present invention includes: a sampling line for sampling the exhaust gas flowing through an exhaust pipe to be introduced into an analyzing instrument; a plurality of heating parts provided along the sampling line from an upstream side to a downstream side for heating the exhaust gas flowing through the sampling line; and a temperature control part for individually defining setting temperatures of the plurality of heating parts using the temperature of the exhaust gas in the exhaust pipe and a target temperature of the exhaust gas in an outlet side of the heating part located in the most downstream among the plurality of heating parts as parameters.

With this configuration, since a plurality of heating parts are provided along the sampling line and the setting temperatures of the plurality of heating parts are individually defined using the temperature of the exhaust gas in the exhaust pipe and a target temperature of the exhaust gas in the outlet side of the heating part located in the most downstream as parameters, it is possible to heat or cool a temperature of sampled exhaust gas flowing through the sampling line to be a desired temperature irrespective of a temperature of the exhaust gas flowing through the exhaust pipe. For example, in the sampling line, it is possible to form various temperature gradients along the sampling line from the upstream side to the downstream side by the plurality of heating parts. In addition, even in the case where a possible temperature range of the exhaust gas is over a wide range due to various exhaust gas conditions, by heating or cooling the exhaust gas temperature to be a desired temperature by the plurality of heating parts, the exhaust gas temperature can be controlled to be an exhaust gas target temperature in the outlet side of the heating part located in the most downstream so that the exhaust gas temperature can be adjusted in accordance with the usage conditions and the like of the sampling line.

In addition, in the configuration where one heating part is provided on the sampling line to heat or cool the exhaust gas, the exhaust gas can be heated or cooled to an exhaust gas target temperature by defining the setting temperature to be the exhaust gas target temperature. However, after the exhaust gas is heated or cooled to a predetermined temperature (first temperature), it is impossible to heat or cool the exhaust gas to be the exhaust gas target temperature (second temperature). In addition, although it can be considered that a single temperature gradient is formed using one heating part by controlling a winding density of a heater coil and the like to thereby heat or cool the exhaust gas to a target temperature, if the temperature gradient is single, the temperature to be heated or cooled by the heating part in accordance with the temperature of the exhaust gas flowing into the heating part is determined, and therefore it is difficult to obtain a desired temperature in some cases.

In the case where the exhaust gas temperature is lower than the exhaust gas target temperature, there is a problem that a deposition reaction of predetermined components contained in the exhaust gas does not proceed sufficiently only by heating the corresponding exhaust gas temperature to be an exhaust gas target temperature. Therefore, in the case where the exhaust gas temperature is lower than the exhaust gas target temperature, it is desirable that the temperature control part defines the setting temperature of the heating part located in the most upstream to be a temperature higher than the exhaust target temperature. With this configuration, since the setting temperature of the heating part located in the most upstream is defined to be a temperature higher than the exhaust target temperature, the exhaust gas temperature is once adjusted to be a temperature higher than the exhaust gas target temperature so that the decomposition reaction of the predetermined components contained in the exhaust gas is allowed to proceed sufficiently and then the exhaust gas can be introduced into such as an analyzing instrument.

In such a case where, for example, an optimality examination of urea injection in an urea SCR system is performed specifically using the exhaust gas sampling device of the present invention, it is desirable that the exhaust gas includes urea and/or a decomposition component derived from urea, and the setting temperature of the heating part located in the most upstream is a temperature equal to or higher than a hydrolysis temperature of isocyanate produced by thermal decomposition of the urea. With this configuration, since the isocyanate (HNCO) produced by thermal decomposition of the urea can be hydrolyzed in the sampling line, it is possible to improve measurement accuracy of ammonia ($NH_3$) produced by urea. Therefore, the optimality examination of injection of urea for example, in the urea SCR system can be accurately performed.

In addition, cyanuric acid may be possibly produced by thermal decomposition of urea under some temperature rise conditions of urea. In order to decompose this cyanuric acid into isocyanate so that the isocyanate is hydrolyzed as described above, it is desirable that the setting temperature of the heating part located in the most upstream is a temperature equal to or higher than a decomposition temperature of decomposing cyanuric acid produced by thermal decomposition of the urea into isocyanate.

It is desirable that, the sampling line is provided with an adiabatic expansion part for adiabatically expanding the exhaust gas flowing through the corresponding sampling line, the plurality of heating parts are provided in an upstream side than the adiabatic expansion part, the adiabatic expansion part includes a throttle part for decompressing the exhaust gas flowing through the sampling line and a temperature adjustment part for adjusting a temperature of the exhaust gas that has passed through the corresponding throttle part, and the temperature control part individually defines the setting temperatures of the plurality of heating parts using the exhaust gas temperature and the exhaust gas target temperature at the throttle part as the parameters. By decompressing and heating the exhaust gas by the throttle part and the temperature adjustment part in this way, condensation of a predetermined component (for example, hydrocarbon) contained in the exhaust gas that has passed through the throttle part can be prevented. Further, since the temperature at the throttle part is used as the exhaust gas target temperature, in such a case where a plurality of analyzing instruments are connected via the throttle part, the target exhaust gas temperature at the throttle part is defined to be, for example, that of the analyzing instrument having the highest usage temperature among the plurality of analyzing instruments, whereby the exhaust gas sampling device of the present invention can be used for the plurality of analyzing instruments. Further, at this time, since the decompression and heating are performed by the throttle part and the temperature adjustment part, the exhaust gas can be introduced into a predetermined analyzing instrument with the temperature thereof made lower than the target exhaust gas temperature at the throttle part.

More specifically, in the case where the exhaust gas sampling device of the present invention is used in a measurement system of hydrocarbon, there is a problem that the corresponding hydrocarbon is condensed so that ammonia would be adsorbed to the corresponding hydrocarbon. Therefore, it is desirable that the exhaust gas target temperature at the throttle part is a temperature higher than a condensation temperature of HC contained in the exhaust gas. Further, since the exhaust gas is expanded by the adiabatic expansion part, the exhaust gas temperature can be lowered to a measurement temperature of the $NH_3$ analyzer while the condensation of the hydrocarbon is prevented.

Advantageous Effects of Invention

According to the present invention configured as described above, since it is possible to heat or cool the sampled exhaust gas flowing through a sampling line to a desired temperature irrespective of a temperature of the exhaust gas flowing through an exhaust pipe and various temperature gradients can be formed by individually defining the setting temperatures of the plurality of heating parts, it is possible to provide an exhaust gas sampling device that can be used in various applications capable of providing such as a decomposition a predetermined component contained in the exhaust gas can be sufficiently proceeded.

DESCRIPTION OF EMBODIMENTS

The following describes an exhaust gas measurement system using an exhaust gas sampling device 100 according to the present invention with reference to the accompanying drawings.

The exhaust gas measurement system of the present embodiment is intended to measure a predetermined component contained in the exhaust gas discharged from an internal combustion engine such as, for example, a diesel engine.

Figure 1:
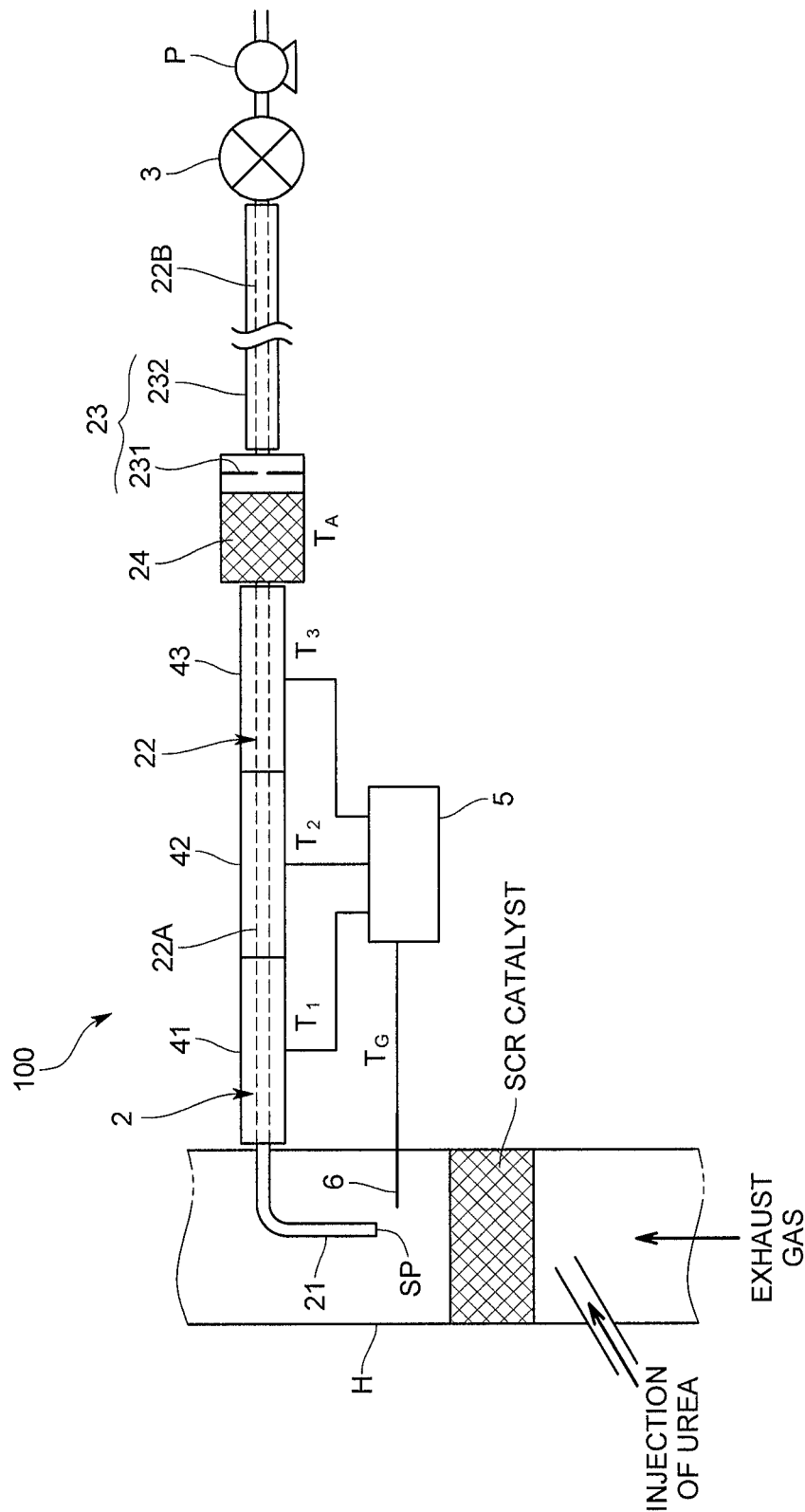
FIG. 1 is a schematic diagram of an exhaust gas measurement system using an exhaust gas sampling device of the present embodiment.

Specifically, as shown in FIG. 1, this exhaust gas measurement system includes: a sampling line 2 which is equipped with a sampling port SP inside an exhaust pipe H to introduce the exhaust gas taken by the corresponding sampling port SP into an analyzing instrument 3; a plurality of heating parts 41 to 43 (three in the present embodiment) provided along the corresponding sampling line 2 from an upstream side to a downstream side for heating the exhaust gas flowing through the sampling line 2; and a temperature control part 5 for individually defining setting temperatures of the respective plurality of heating parts 41 to 43 using an exhaust gas temperature $T_G$ (a temperature of the exhaust gas at a sampling point (in the vicinity of the sampling port SP)) in the exhaust pipe H and an exhaust gas target temperature $T_A$ at an outlet side of the heating part 43 located in the most downstream among the plurality of heating parts 41 to 43 as parameters.

In this configuration, the analyzing instrument 3 of the present embodiment is an $NH_3$ analyzer for measuring a concentration of ammonia contained in the exhaust gas by an absorptiometric method using a laser beam. The $NH_3$ analyzer is provided with: a measuring cell; a laser beam irradiation part for introducing a laser beam through a light introduction window of this measuring cell and irradiating a laser beam with high linearity to the sample gas in the measuring cell; a light detecting part that detects the laser beam transmitted out of the measuring cell; and a decompression pump (pump P located in a downstream side of the sampling line 2) connected to the measuring cell to decompresses inside the measuring cell. Here, with use of a multiple reflection typed measuring cell, even though ammonia is of a low concentration, the detection sensitivity thereof can be increased. In addition, the laser beam irradiation part is intended to emit a laser beam having a wavelength of an infrared region such as a middle infrared region or a near-infrared region or an oscillation wavelength of an ultraviolet region in which the $NH_3$ has absorption characteristics and it is considered to use, for example, a quantum cascade laser, a semiconductor laser such as a wavelength tunable semiconductor laser, a solid laser or a liquid laser. As the light detection part, it is considered to use, for example, MCT (HgCdTe) detector of a room temperature operation type. The decompression pump decompresses inside the measuring cell, for example, to 1 kPa (a pressure at which the gas concentration becomes too small so that the measurement becomes difficult) to 50 kPa (a pressure at which a peak becomes gentle and becomes easy to occur interference with the other gas components), and preferably decompresses to 20 kPa to 30 kPa which is in a pressure range where the absorption of $NH_3$ is less likely to occur, and there occurs no interference with further another gas component while achieving a measurable gas concentration.

The sampling line 2 includes: a sampling unit 21 which is provided inside the exhaust pipe H to take a part of the exhaust gas flowing through the exhaust pipe H by a sampling port SP; and a sampling piping 22 which is connected to the sampling unit 21 to introduce the sampled exhaust gas into the analyzing instrument 3.

The sampling piping 22 is provided with a throttle part (for example, an orifice) 231 that constitutes an adiabatic expansion part 23 for adiabatically expanding the sampled exhaust gas to be decompressed and cooled. There is further provided a filter 24 in the immediate vicinity of the upstream side of the throttle part 231 for removing soot and the like in the exhaust gas. And the sampling piping 22 is divided into an upstream side piping 22A located in the upstream side of the throttle part 231 and the filter 24 and a downstream side piping 22B located in the downstream side of the throttle part 231 and the filter 24. A plurality of heating parts 41 to 43 are provided on the upstream side piping 22A, and a temperature adjustment part 232 such as a heating pipe constituting the adiabatic expansion part 23 is provided on the downstream side piping 22B for keeping the downstream side piping 22B at a constant temperature (113° C. which is the usage temperature of the $NH_3$ analyzer 3 in the present embodiment). In this configuration, since the throttle part 231 is provided on the sampling line 2, a residence time of the exhaust gas in the upstream side piping 22A can be increased.

The plurality of heating parts 41 to 43 are provided on the upstream side piping 22A located in the upstream side of the throttle part 231 and the filter 24. Each of the heating parts 41 to 43 is a coil shaped or cylindrical shaped heater provided on the outer surface of the upstream side piping 22A, and this heater is adjusted to be a predetermined temperature by controlling a current value of current supplied by a temperature control part 5 to be described later. In addition, the plurality of heating parts 41 to 43 are provided over the whole part of the upstream side piping 22A, and each of the heating parts 41 to 43 is entirely provided over each of the multiple regions obtained by equally dividing the upstream side piping 22A. By providing the heating parts 41 to 43 in this way, the heating or cooling of the exhaust gas is facilitated.

The temperature control part 5 is composed of such as a PID controller, which is provided in the vicinity of the sampling port SP inside the exhaust pipe H so that an exhaust gas temperature $T_G$ is acquired from a temperature sensor 6 for detecting the exhaust gas temperature $T_G$ at the corresponding sampling point. In this temperature control part 5, a predetermined exhaust gas target temperature $T_A$ at an outlet side of the heating part 43 located in the most downstream is inputted. In the present embodiment, the exhaust gas target temperature $T_A$ is an exhaust gas target temperature of the exhaust gas flowing into the adiabatic expansion part 23 and this exhaust gas target temperature is 190° C. which is higher than the condensation temperature of the hydrocarbon (HC) contained in the exhaust gas.

And the temperature control part 5 individually defines the setting temperatures $T_1$ to $T_3$ of the plurality of heating parts 41 to 43, respectively, using the exhaust gas temperature $T_G$ and the exhaust gas target temperature $T_A$ as parameters and then controls the current flowing through the respective heating parts 41 to 43 so that the heating temperatures of the respective heating parts 41 to 43 made equal to the setting temperatures $T_1$ to $T_3$.

Figure 2:
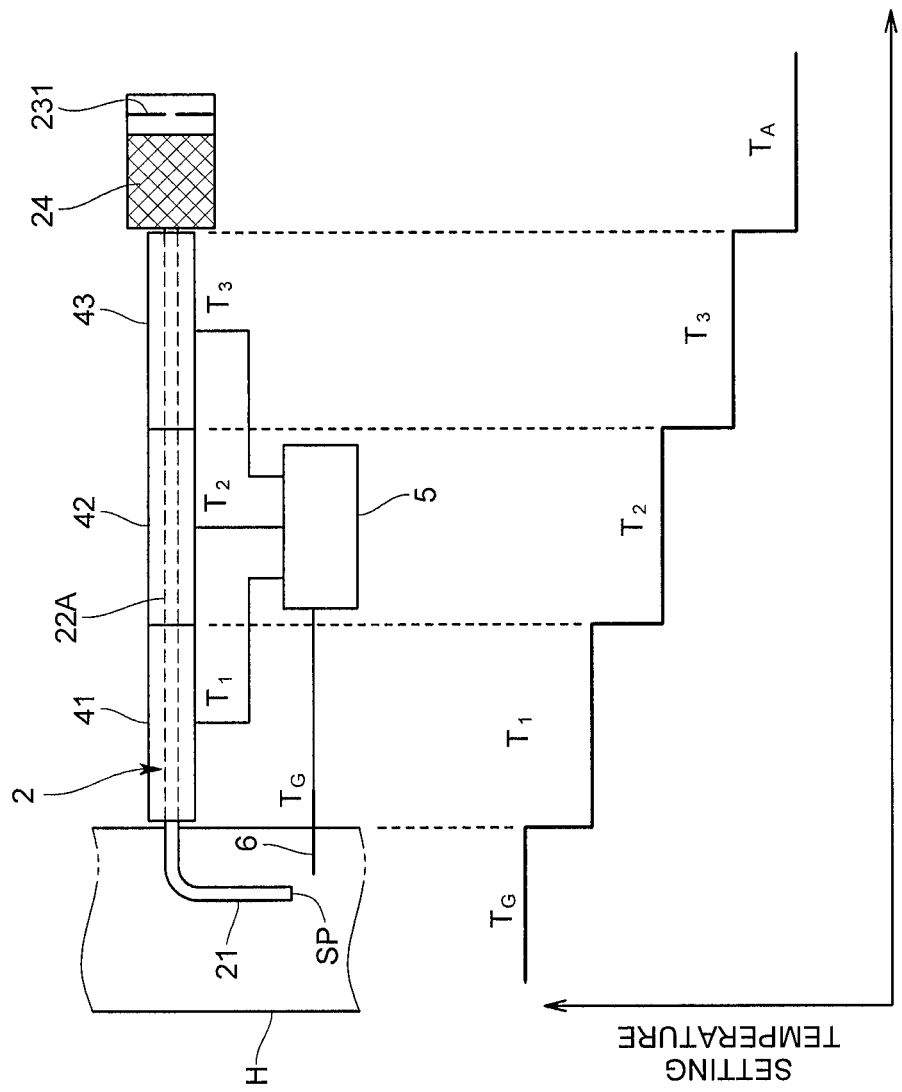
FIG. 2 is a diagram showing an example of setting temperatures of the exhaust gas sampling device of the same embodiment.

Specifically, as shown in FIG. 2, in the case where the exhaust gas temperature $T_G$ is higher than the exhaust gas target temperature $T_A$, the temperature control part 5 defines the setting temperatures $T_1$ to $T_3$, for example, in a manner as follows:

$$T_3 = T_A + (T_G - T_A)/4$$

$$T_2 = T_3 + (T_G - T_A)/4$$

$$T_1 = T_2 + (T_G - T_A)/4$$

In this way, the temperature control part 5 defines the temperatures obtained by equally dividing the difference between the exhaust gas temperature $T_G$ and the exhaust gas target temperature $T_A$ to be used as the setting temperatures $T_1$ to $T_3$ of the respective heating parts 41 to 43. By changing the temperature of the sampled exhaust gas in a stepwise manner at the same rate of change in this way, the temperature of the sampled exhaust gas is prevented from rapidly changing, thereby avoiding such as condensation of the predetermined components contained in the exhaust gas.

Figure 3:
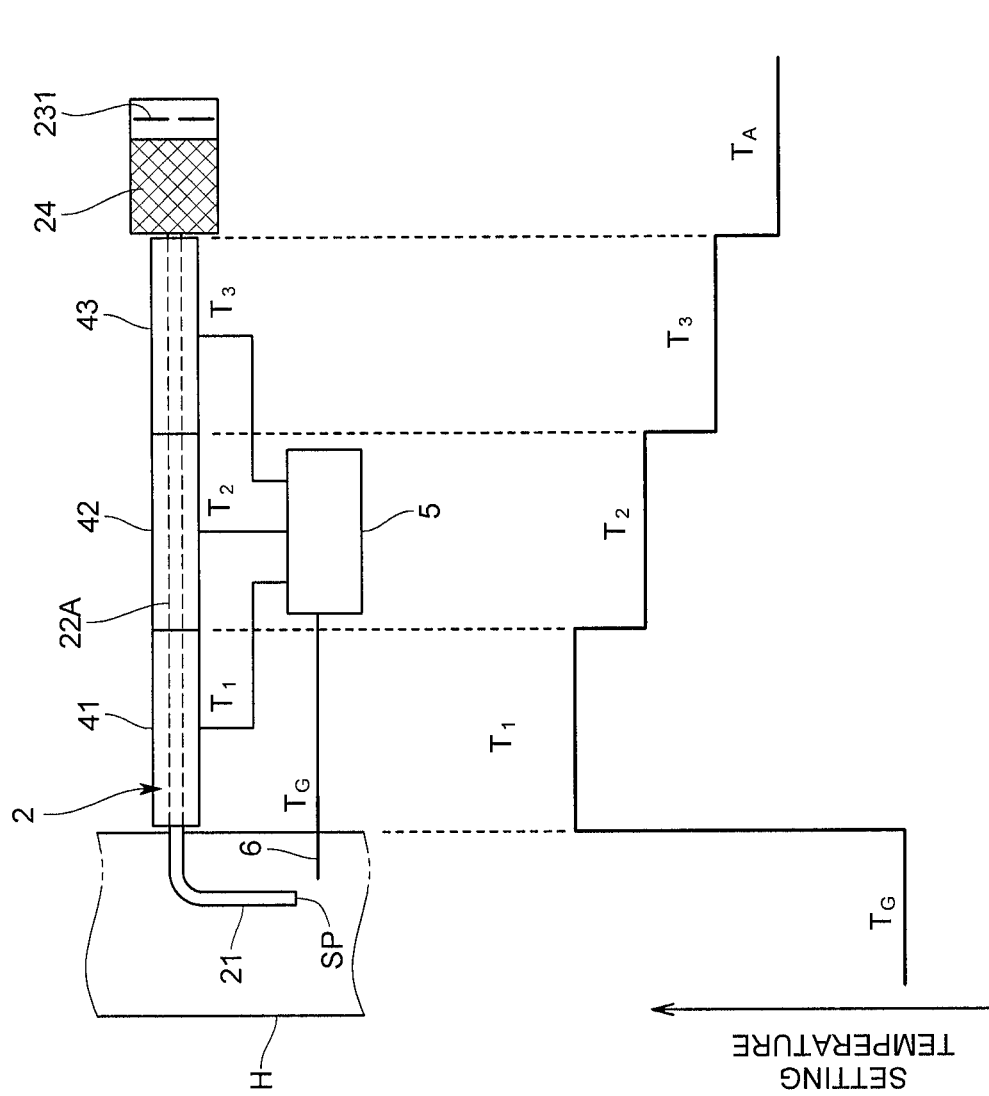
FIG. 3 is a diagram showing an example of setting temperatures of the exhaust gas sampling device of the same embodiment.

On the other hand, as shown in FIG. 3, in the case where the exhaust gas temperature $T_G$ is lower than the exhaust gas target temperature $T_A$, the setting temperature $T_1$ of the heating part 41 located in the most upstream is defined to be a temperature higher than the exhaust gas target temperature $T_A$ (=190° C.). More specifically, the setting temperature $T_1$ of the heating part 41 located in the most upstream is defined to be equal to or higher than 300° C. This temperature 300° C. is the decomposition temperature of decomposing cyanuric acid produced by thermal decomposition of urea to isocyanate. Thus, by defining the setting temperature of the heating part 41 located in the most upstream is defined to be equal to or higher than the decomposition temperature, the amount of ammonia produced from the urea can be increased as much as possible so that the measurement accuracy of the concentration of ammonia can be improved.

Then, the setting temperature $T_2$ of the second heating part 42 and the setting temperature $T_3$ of the third heating part 43 are defined, for example, in a manner as follows:

$$T_3 = T_A + (T_1 - T_A)/3$$

$$T_2 = T_3 + (T_1 - T_A)/3$$

In this way, the temperature control part 5 defines the temperatures obtained by equally dividing the difference between the setting temperature $T_1$ and the exhaust gas target temperature $T_A$ to be used as the setting temperatures $T_2$ and $T_3$ of the respective second and third heating parts 42 and 43.

In either case described above (i.e., in the case where the exhaust gas temperature $T_G$ is higher/lower than the exhaust gas target temperature $T_A$), the setting temperatures $T_1$ to $T_3$ of the plurality of heating parts 41 to 43 are defined in such a manner that, the temperature of the exhaust gas is changed in the temperature range including the whole temperatures of: the thermal decomposition temperature (132° C.) of urea; hydrolysis temperature (160° C.) of isocyanate produced by thermal decomposition of urea; and thermal decomposition temperature (equal to or higher than 300° C.) of cyanuric acid produced by thermal decomposition of urea, until the exhaust gas temperature $T_G$ is heated or cooled to the exhaust gas target temperature $T_A$.

It is noted here that, in the case where the exhaust gas temperature $T_G$ is lower than the exhaust gas target temperature $T_A$, the setting temperatures $T_1$ to $T_3$ of the first to third heating parts 41 to 43 may be defined to be equal to the exhaust gas target temperature $T_A$ (190° C.) so that the temperature of the sampled exhaust gas that has passed through the upstream side piping 22A of the sampling line 2 becomes the exhaust gas target temperature $T_A$.

Figure 4:
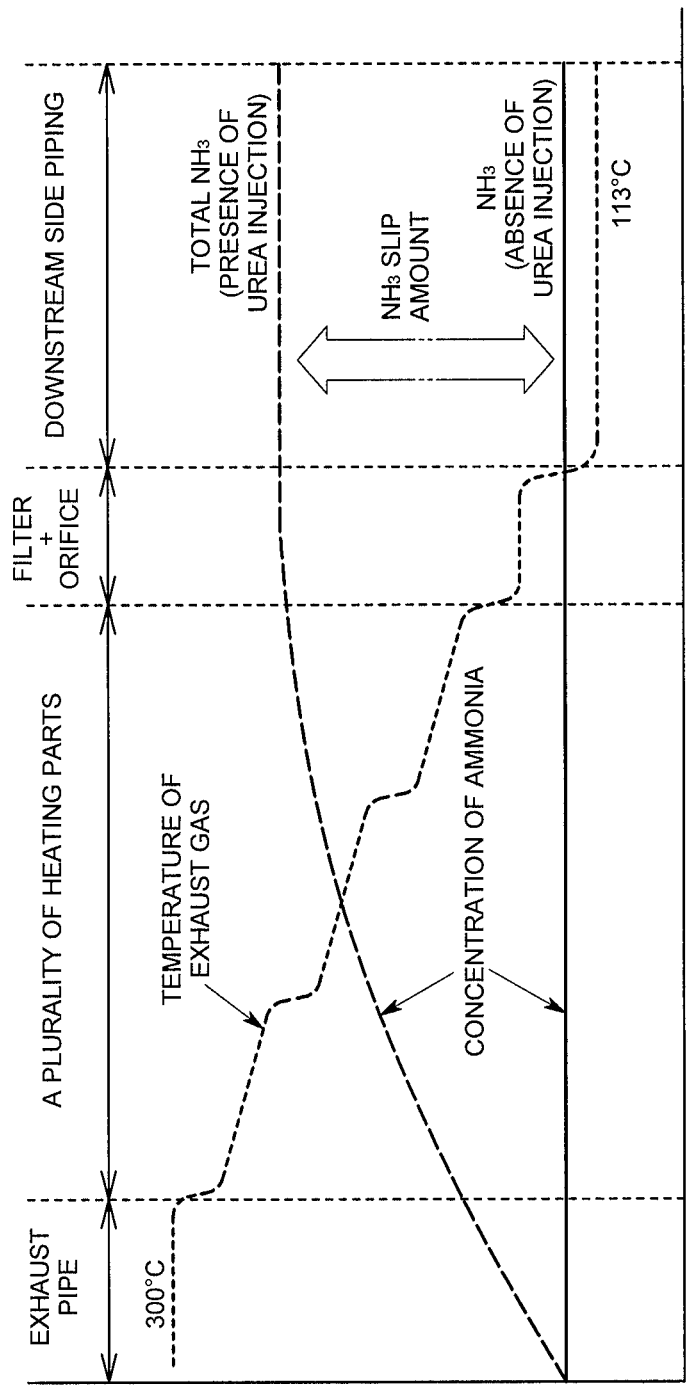
FIG. 4 is a schematic diagram showing an ammonia concentration in the exhaust gas in the case of presence or absence of urea injection of the same embodiment.

Next, the following describes a change of the concentration of ammonia obtained by the $NH_3$ analyzer 3 in the case where urea is injected or urea is not injected in the urea SCR system by the exhaust gas measurement system using the exhaust gas sampling device 100 configured as described above with reference to FIG. 4.

In the case where urea is not injected, the concentration of the $NH_3$ obtained by the $NH_3$ analyzer 3 is a concentration of raw $NH_3$ originally contained in the exhaust gas discharged from the internal combustion engine. Since ammonia is not thermally decomposed even though heated in the sampling line, in the case where there is no absorption or the like of ammonia to an inner surface of the sampling line, the concentration of the $NH_3$ contained in the exhaust gas flowing through the exhaust pipe is equal to the concentration of the $NH_3$ obtained by the $NH_3$ analyzer 3.

On the other hand, in the case where urea is injected, the concentration of the $NH_3$ obtained by the $NH_3$ analyzer 3 is equal to a concentration of the $NH_3$ obtained by adding excessive $NH_3$ which could not have been reacted with $NO_x$ by a SCR catalyst and $NH_3$ produced by thermal decomposition and hydrolysis of the urea contained in the sampled exhaust gas in addition to the concentration of the raw $NH_3$. By injecting urea in this way, there occurs an ammonia slip (ammonia emission).

As described above, since the concentrations of $NH_3$ are different depending on presence or absence of injection of urea, the concentration of $NH_3$ caused by an urea SCR can be calculated based on a difference between the concentrations of the $NH_3$ obtained by these two measurements so that the evaluation of the urea SCR system can be properly performed.

According to the exhaust gas measurement system according to the present embodiment configured as described above, since the plurality of heating parts 41 to 43 are provided along the sampling line 2 and the setting temperatures of the plurality of heating parts 41 to 43 are individually defined using the temperature $T_G$ of the exhaust gas in the exhaust pipe H and a target temperature $T_A$ of the exhaust gas in the outlet side of the heating part 43 located in the most downstream as parameters, it is possible to heat or cool a temperature of sampled exhaust gas flowing through the sampling line 2 to be a desired temperature irrespective of a temperature of the exhaust gas flowing through the exhaust pipe H. For example, in the sampling line, it is possible to form various temperature gradients along the sampling line from the upstream side to the downstream side, for example, a temperature gradient falling down from the upstream side to the downstream side, a temperature gradient rising up from the upstream side to the downstream side, a mountain like sloped temperature gradient and the like by the plurality of heating parts 41 to 43. In addition, even in the case where a possible temperature range of the exhaust gas temperature $T_G$ is over a wide range due to various exhaust gas conditions, by heating or cooling the exhaust gas temperature $T_G$ to be a desired temperature by the plurality of heating parts 41 to 43, the exhaust gas temperature $T_G$ can be controlled to be an exhaust gas target temperature $T_A$ so that the exhaust gas temperature $T_G$ can be adjusted in accordance with the usage conditions and the like of the filter 24, adiabatic expansion part 23 or the analyzing instrument 3 etc. provided on the sampling line 2.

In particular, in the case where the exhaust gas temperature $T_G$ is lower than the exhaust gas target temperature $T_A$, since the setting temperature $T_1$ of the heating part 41 located in the most upstream is defined to be equal to or higher than 300° C. which is higher than the exhaust gas target temperature $T_A$ (=190° C.), not only the isocyanate (HNCO) produced by thermal decomposition of urea can be hydrolyzed in the sampling line 2 but also the cyanuric acid produced by thermal decomposition of urea can be thermally decomposed to isocyanate and the corresponding isocyanate can be hydrolyzed in the sampling line 2, the concentration of ammonia derived from urea can be accurately measured.

Since the gas pressure inside the measuring cell and in the flow passage from the downstream side of the throttle part 231 to the measuring cell are decompressed by the pump P, a region to be decompressed in the flow passage connected to the measuring cell can be enlarged and the absorption of absorptive gas components such as $NH_3$ or HC can be reduced. Thus, even though the gas component having absorptive characteristics such as $NH_3$ or HC is low in concentration, the concentration can be accurately measured and a response speed of measuring the concentration can be improved. Moreover, the decompressed sampling gas is to be heated by the temperature adjustment part 232 and therefore a loss of dissolved gas of the absorptive gas components caused along with condensation inside the pipe can be prevented so that the measurement accuracy and the response speed can be further improved. Furthermore, when an absorption spectrum in a normal pressure is observed, it is known that an absorption peek has an extent. However, by rendering the inside of the measuring cell to be in a decompressed state, a sharp peak can be obtained so that an interference influence on the absorption peak of $NH_3$ can be reduced.

It is noted that the present invention should not be limited to the embodiment described above.

Figure 5:
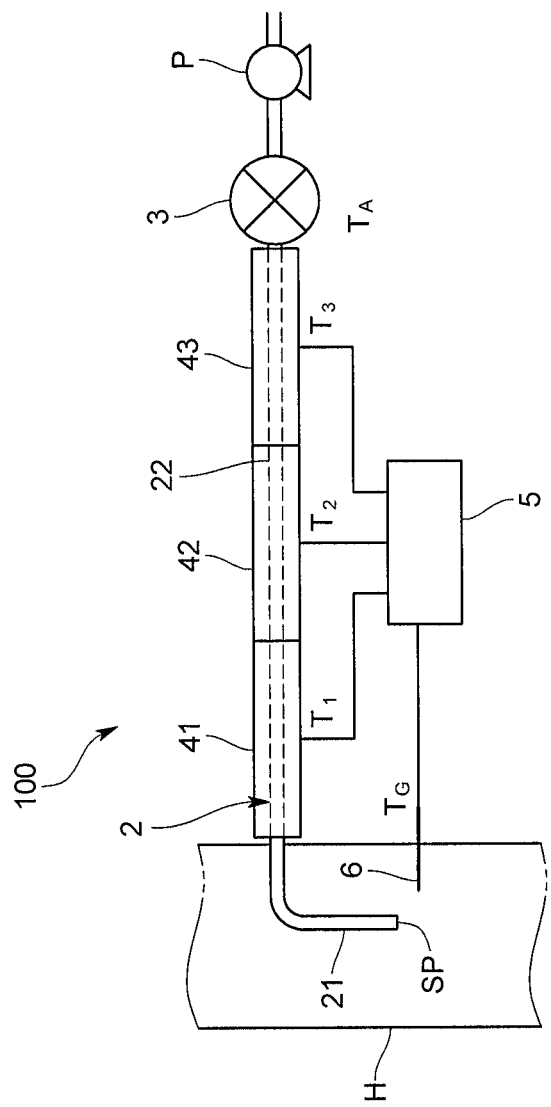
FIG. 5 is a schematic diagram of an exhaust gas measurement system of a modified embodiment.

For example, although the exhaust sampling device 100 includes the adiabatic expansion part 23 in order to be commonly used for a plurality of components (such as HC and $NH_3$) to be measured in the above embodiment, the sampled exhaust gas may be directly introduced into the analyzing instrument 3 without the adiabatic expansion part 23 as shown in FIG. 5. In this case, when ammonia contained in the exhaust gas is measured, the exhaust gas target temperature is, e.g., 113° C. because the analyzing instrument is composed of an $NH_3$ analyzer as in the above embodiment.

In addition, although the exhaust gas measurement system includes the $NH_3$ analyzer in the above embodiment, a plurality of other analyzers for measuring various components contained in the exhaust gas may be included in the exhaust gas measuring system. In this case, the plurality of analyzers may be arranged in series on the sampling line 2, or the downstream side pipe of the sampling line 2 may be branched into a plurality of flow passages so that each of the analyzers is arranged on each of the branched flow passages.

In addition, the present invention should not be limited the present embodiment, and it is needless to say that various modifications are of course possible within the scope unless departing from the intended spirit thereof.

DESCRIPTION OF REFERENCE NUMERALS

100 . . . Exhaust gas sampling device
H . . . Exhaust pipe
2 . . . Sampling line
21 . . . Sampling unit
22 . . . Sampling piping
23 . . . Adiabatic expansion part
231 . . . Throttle part (orifice)
232 . . . Temperature adjustment part (heating tube)
3 . . . Analyzing instrument ($NH_3$ meter)
P . . . Pump
41 . . . First heating part (heating part located in the most upstream)
42 . . . Second heating part
43 . . . Third heating part (heating part located in the most downstream)
$T_G$ . . . Exhaust gas temperature
$T_A$ . . . Exhaust gas target temperature
$T_1$ . . . Setting temperature of the first heating part
$T_2$ . . . Setting temperature of the second heating part
$T_3$ . . . Setting temperature of the third heating part
5 . . . Temperature control part

What is claimed is:

1. An exhaust gas sampling device comprising:
a sampling conduit having an inlet and an outlet, and configured to sample exhaust gas flowing through an exhaust pipe via the inlet;
a plurality of heaters provided along the sampling conduit from the inlet to the outlet and configured to heat exhaust gas flowing through the sampling conduit; and
a controller programmed to define, for each of the heaters, a set temperature for the heater based on a temperature of exhaust gas at a sampling point in the exhaust pipe and a target temperature for exhaust gas exiting the outlet such that the set temperatures are different, and to operate the heaters based on the set temperatures to form a temperature gradient along the sampling conduit.

2. The exhaust gas sampling device according to claim 1, wherein the controller is further programmed to, in response to the temperature of exhaust gas flowing through the exhaust pipe being less than the target temperature, define the set temperature for the heater located closest to the inlet to be greater than the temperature of exhaust gas flowing through the exhaust pipe.

3. The exhaust gas sampling device according to claim 1, wherein the set temperature of the heater located closest to the inlet is greater than or equal to a hydrolysis temperature of isocyanate produced by thermal decomposition of urea in exhaust gas flowing through the exhaust pipe.

4. The exhaust gas sampling device according to claim 3, wherein the set temperature of the heater located closest to the inlet is greater than or equal to a decomposition temperature of decomposing cyanuric acid produced by thermal decomposition of the urea into isocyanate.

5. The exhaust gas sampling device according to claim 1 further comprising an adiabatic expander, including a throttle and heating pipe, arranged with the sampling conduit such that the heaters are disposed between the inlet and adiabatic expander, wherein the controller is further programmed to define the set temperatures based on a temperature of exhaust gas flowing through the throttle.

6. The exhaust gas sampling device according to claim 5, wherein a target temperature at the throttle is greater than a condensation temperature of HC contained in exhaust gas under a throttled pressure.

* * * * *